United States Patent [19]

Schutt

[11] 4,357,311

[45] Nov. 2, 1982

[54] SUBSTRATE FOR IMMUNOASSAY AND MEANS OF PREPARING SAME

[75] Inventor: Ernest G. Schutt, Long Valley, N.J.

[73] Assignee: Warner-Lambert Company, Morris Plains, N.J.

[21] Appl. No.: 193,789

[22] Filed: Oct. 3, 1980

[51] Int. Cl.³ .................. C07D 251/02; C07L 1/12; C07L 89/00; G01N 33/52

[52] U.S. Cl. .................. 424/12; 23/230 B; 260/112 R; 424/8; 424/13; 424/78; 424/180; 435/7; 435/179; 435/181; 544/217; 525/54.1; 521/53

[58] Field of Search ............... 424/8, 12, 13, 78, 180; 23/230 B; 435/7, 177, 179, 181; 260/6, 8, 112 R; 536/58, 63, 72, 75; 544/217

[56] References Cited

U.S. PATENT DOCUMENTS 3,619,371 11/1971 Crook .................. 435/181
3,824,150 7/1974 Lilly .................. 435/178
4,007,089 2/1977 Smith .................. 435/181
4,119,494 10/1978 Durand .................. 435/176
4,229,537 10/1980 Hodgins .................. 435/177

FOREIGN PATENT DOCUMENTS 52-52983 4/1977 Japan .
WO79/00609 8/1979 PCT Int'l Appl. .

OTHER PUBLICATIONS

Zerlotti, Nature, vol. 214, Jun. 24, 1967, pp. 1304–1306.

Primary Examiner—Anna P. Fagelson
Attorney, Agent, or Firm—Albert H. Graddis

[57] ABSTRACT

A method is disclosed for preparing an activated microporous substrate to which antibody may be covalently bonded through trichloro-triazine to yield an activated substrate which is very useful for many immunochemical reactions utilizing a flow-through procedure.

7 Claims, No Drawings

SUBSTRATE FOR IMMUNOASSAY AND MEANS OF PREPARING SAME

BACKGROUND OF THE INVENTION

This invention relates to an improved method for the coupling of antibodies to a solid phase polymeric substrate having hydroxy groups present through strong covalent chemical bonds formed by trichloro-triazine as the linking agent between the substrate and antibody. This invention also relates to the use of this substrate in immunoassay procedures for the quantitative and qualitative determination of minute quantities of various substances in body fluids such as blood, urine, saliva, etc. These immunoassay procedures may rely upon the detection and measurement of various levels of radioactivity, enzyme activity or of fluorescence in making a determination of the substances being assayed.

The use of trichloro-triazine in a procedure for covalently coupling various substances to solid substrates under anhydrous conditions for the production of solid phase catalysts and certain biospecific adsorbents is disclosed in U.S. application Ser. No. 876,240, filed Feb. 9, 1978, now U.S. Pat. No. 4,229,537.

This application has been published under International Publication No. WO 79/00609 on Aug. 23, 1979, together with an International Search Report dated May 15, 1979. These publications including the art cited are incorporated herein by reference.

The coupling or bonding of enzymes to an insoluble support sheet through an s-triazine bridge to produce an immobilized enzyme is described in U.S. Pat. No. 3,824,150. An analogous method for linking biologically active compounds to various carriers through an asymmetric bifunctional linking compound which includes an s-triazine moiety in the linking compound is disclosed in U.S. Pat. No. 4,007,089. The direct fixation of enzymes on solid support materials employing temperatures of 60° C. to 120° C. and an anhydrous organic liquid medium for the reaction is described in U.S. Pat. No. 4,119,494. The support materials disclosed are widely diverse and include, among others, brick, clay, sand, starch, cellulose, and various synthetic organic polymers such as polystyrene and polybutadiene, as well as copolymers of methacrylic acid. Antimicrobial compounds can be bound to a hydroxyl bearing substrate such as cellulose, starch or leather, for example, through an s-triazine bond in alkaline solution at a pH of 9 to 10 by following the procedureds described in U.S. Pat. No. 4,035,146. Cellulosic fabrics having persistent antimicrobial activity may be obtained. Various procedures have been disclosed for forming the initial s-triazine bond with the solid phase substrate or support and then coupling the activated substrate obtained with any one of several biologically active compounds. As disclosed in the patents cited above these compounds may include enzymes, antimicrobials, antigens, antibodies, haptens, etc. Depending upon the particular biologically active compound which is bound to the substrate, the resulting solid phase substrate may be employed in a wide variety of biochemical procedures including highly sensitive quantitative immunological and analytical procedures in blood chemistry. Nanogram quantities of various substances can readily be detected utilizing radio-immunoassay, enzyme immunoassay and fluorescent immunoassay techniques. The use of an activated solid phase substrate greatly simplifies these test procedures.

Of particular value for use in such immunoassay techniques are the said substrates comrising microporous membrane filters which have been activated by being coupled through an s-triazine covalent bond to a biologically active compound. Such activated materials can be produced in discrete physical forms which lend themselves quite readily to flow-through assay techniques. Here, the body fluid being tested whether blood serum, blood plasma, urine, etc. actually flows through the test system in contact with the activated surfaces of the membrane filter when carrying out the test procedure. These membrane filters are available in a range of pore sizes so that varying flow rates and contact times can be achieved within the parameters of the particular immunoassay test being used.

By coupling the activated solid phase substrate to a desired biologically active compound a wide range of immunoassay test procedures and techniques may be put to use.

SUMMARY OF THE INVENTION

The invention comprises treating a dry microporous filter membrane formed of a polymeric material having free and esterified hydroxy groups in the polymer to hydrolyze some of the ester groups, converting at least some of the free hydroxy groups present to the corresponding alkali metal hydroxylate and then reacting the alkali metal hydroxylate compound with trichlorotriazine. The alkali metal halide formed during the reaction may be separated. Removal of the solvent from the solid substrate leaves an activated substrate which is available for further reaction with a biologically active compound.

DETAILED DESCRIPTION OF THE INVENTION

As examples of microporous filter membranes suitable for activation in accordance with the process described there may be mentioned those containing free and esterified hydroxy groups and formed of cellulose esters such as cellulose nitrate cellulose acetate, cellulose propionate and cellulose butyrate as well as those formed of mixed cellulose esters such as cellulose acetate-propionate and cellulose acetate-butyrate. These filter membranes and particularly those having a base of cellulose acetate are available in wide range of pore sizes which typically can vary from 0.2 m to 100 m in average diameter.

Swelling the microporous cellulose ester filter membrane with an anhydrous organic solvent system prior to hydrolysis which preferably comprises anhydrous methanol and an inert solvent such as $CCl_4$, $CFCl_3$, $CCl_2F_2$, $CCl_2F_2$ yields an improved result. The methanol can comprise up to about 40% by volume of the solvent system. In order to hydrolyze some of the ester groups and convert some of the free hydroxy groups in the swollen cellulose ester filter membrane to the corresponding alkali metal hydroxylate the swollen cellulose ester filter membrane is then treated with a solution which preferably comprises anhydrous methanol and sodium methoxide in an inert solvent, such as those described above. Employing carbon tetrachloride as the inert solvent the solution is preferably formed by adding 0.1 to 20 ml of a 1 to 250 mg/ml solution of sodium methoxide in anhydrous methanol to each 100 ml of carbon tetrachloride. Trichlorofluoromethane is an equally useful inert solvent.

The partial hydrolysis of the ester groups present on the cellulose ester filter membrane substrate is effected by passing the sodium methoxide solvent solution over or through the filter membrane. Contact times of from 15 to 200 seconds are suitable in order to reach the desired degree of hydrolysis whereby the cellulose ester retains an average of from about 1% to about 98% esterified hydroxy groups. Preferably at least 90% of the esterified hydroxy groups are retained. The partial hydrolysis reaction is preferably carried out at a temperature of from about −10° to 15° C.

To ensure removal of any free sodium methoxide the hydrolyzed substrate is washed several times with the inert solvent employed.

To react the hydrolyzed substrate with trichlorotriazine, a mixture of trichlorotriazine in an inert solvent is passed over, or through the treated filter membrane and the reaction allowed to proceed at a temperature of −10° to 25° C. A contact time of from 15 to 200 seconds is sufficient. The solution of trichlorotriazine may contain from 0.5 to 200 mg of trichlorotriazine for each ml. of solvent but a concentration of 2.5 mg per ml of solvent allows the reaction to proceed at a desirable rate and to the extent desired to produce an activated substrate. After removal of the inert solvent by washing with diethyl ether, the activated substrate is air-dried and may then be further reacted with a biologically active compound for use as a solid support in immunoassay procedures.

By reacting the activated substrate with a biologically active compound such as the protein which consists of the immune globulin fraction characterized as IgG obtained as part of the antibodies complex raised in goats against rabbit IgG, a basic and extremely useful product having wide application in a variety of immunoassay procedures is obtained. Reaction with the biologically active compound is conveniently effected by incubation of the activated substrate with a buffered solution of the immune globulin fraction.

The desired IgG immune globulin fraction for reaction with the activated substrate can be obtained from antisera available for commercial sources. Goat antirabbit IgG antiserum is an excellent source. This is obtained by bleeding the goats after injecting them with rabbit IgG in a programmed series of injections and separating the blood serum from the other constituents. The desired IgG blood protein fraction can be readily separated from the antiserum obtained by controlled precipitation with aqueous sodium sulfate solution. The known procedures include diluting the antiserum with an equal volume of 18% aqueous sodium sulfate and then precipitating the desired IgG protein fraction by adding sodium sulfate to the diluted serum in an amount of about 180 mg for each ml of original antiserum before dilution. The precipitate of antibody is centrifuged and then washed three times, each time with a volume of aqueous 18% sodium sulfate of about three times the volume of the initial volume of the antiserum. The washed protein fraction of IgG is then dissolved in a volume of distilled water equal to the initial volume of the antiserum and about 0.1% of thimerosal added as a preservative. This solution of antibody in distilled water is used as a stock solution for further processing of the activated substrate.

The coating of the activated substrate with antibody is carried out by incubating the activated substrate in a dilute buffered solution of antibody formed from the stock solution above. The antibody stock solution can be diluted with an equal volume of 1 M phosphate buffer adjusted to a pH of 7.4 and the activated substrate incubated in this buffered solution of antibody for from 4 to 48 hours at a temperature of 0° to 37° C. The 1 M phosphate buffer is prepared as a one molar aqueous solution of monobasic potassium phosphate and is adjusted to a pH of 7.4 with 1 molar sodium hydroxide solution. After incubation, the activated filter membrane substrate which is now coated with antibody is rinsed with distilled water to removal all unbound antibody and placed in 10 mM phosphate buffered saline at pH 7.4 containing about 0.5% by weight ethanolamine, 1% by weight bovine serum albumin and 0.05% by weight of thimerosal and maintained in this solution and room temperature with agitation for 4 to 18 hours. The antibody coated filter membrane can be stored at 4° C. in 0.01 M phosphate buffered saline prior to further use.

In order further to illustrate this invention the following Examples are given:

EXAMPLE 1

A 143 mm diameter cellulose triacetate filter membrane, Gelman TCM-450 Metricel 0.45 $\mu$m pore size, is held for at least 2 hrs. at room temperature in a vacuum desiccator over calcium chloride, in order to dry it. A Gelman glass fiber prefilter (type A/E, 142 mm diameter is dried in the same manner as described above and the dry cellulose triacetate filter membrane together with the dried prefilter is placed in 100 ml of carbon tetrachloride ($CCl_4$) at room temperature containing 20 ml of anhydrous methanol. The membrane filter swells to the desired degree in about 10 seconds.

Both the membrane filter and the profilter are mounted on a Millipore 142 mm filter apparatus with the cellulose triacetate membrane being downstream and the prefilter upstream. The apparatus is equipped with a 1 liter open tank above the filters.

A 40 mm mercury vacuum drop is then applied across the prefilter and membrane filter combination and 200 ml of a 4° C. mixture of $CCl_4$, methanol, and sodium methoxide is gradually pulled through the filter under the action of the vacuum. The solution is made by adding 10 ml of a 25 mg/ml solution of sodium methoxide in methanol to 200 ml of $CCl_4$. When this solution has passed through, the filter is rinsed by allowing 60 ml of $CCl_4$ (at 4° C.) to pass through the filter.

After the rinsing step has been completed 200 ml of a solution of trichloro triazine (cyanuric chloride, MCB-Schuckardt) in $CCl_4$ at 4° C. is pulled through the mounted filters. This solution was made by preparing a stock solution of 50 mg of trichloro triazine per ml of $CCl_4$, filtering it, and then adding 10 ml of the stock solution to 200 ml of $CCl_4$ at 4° C. The filter is then rinsed 3 times by pulling 60 ml of room temperature $CCl_4$ through the filter. The filter is finally rinsed twice with 30 ml of diethyl ether to remove the $CCl_4$ from the filter and to facilitate drying. The trichlorotriazine activated cellulose triacetate filter membrane is removed from the filter apparatus and air dried for 5 minutes. The unactivated edge of the filter disk is then trimmed and the trimmed disk is now ready for reaction with antibody.

EXAMPLE 2

Commercial goat anti-rabbit IgG serum (Antibodies Inc., P-4) is suitably fractionated in order to obtain the desired IgG fraction. This IgG fraction is obtained by diluting the commercial goal anti-rabbit antiserum 1 to 1 with 18% w/v aqueous sodium sulfate and then further dissolving 180 mg of sodium sulfate per ml of antiserum in this mixture. The precipitate obtained is centrifuged at room temperature and at 8,000 G for 30 minutes. The precipitate is then washed by resuspending it in three times the initial antiserum volume of aqueous 18% sodium sulfate solution and again centrifuged at 8000 G. The precipitate obtained is again washed in this manner for a total of 3 times. The thoroughly washed IgG precipitate is then dissolved in a volume of distilled water containing 0.1% thimerosal equal to the original antiserum volume. This solution is used as a stock solution of the IgG fraction goat anti-rabbit IgG in the further treatment of the activated filter membrane.

A 1 to 1 dilution of this stock IgG solution is made with 1 molar phosphate buffer, prepared by adjusting the pH of a 1 molar solution of potassium phosphate, $KH_2PO_4$, with 1 molar sodium hydroxide to pH 7.4. Four ml of this diluted IgG solution is placed in the center of a 145 mm diameter glass Petri dish. The activated disk is then placed on top of this solution and allowed to absorb it for 2 minutes. The disk is then turned over to thoroughly wet the other side. A 145 mm diameter disk of clear plastic wrap (e.g. Saran) is then placed in such position on top of the activated disk and solution as to minimize the amount of air trapped under the clear plastic wrap. The Petri dish is then sealed air-tight with an outer film of clear plastic wrap held in position by means of an elastic band. After a 40 hr. room temperature incubation, the disk is rinsed with distilled water. The disk is then place in a 0.01 molar phosphate buffered saline solution at pH 7.4 containing 0.5% ethanolamine, 1% bovine serum albumin and 0.05% thimerosal for 18 hours at room temperature while applying gentle agitation. The disk is now stored in 0.01 molar phosphate buffered saline containing 0.5% thimerosal prior to use.

The antibody coated filter membranes obtained as described above may be employed for quantitatively determining human blood levels of various therapeutic agents as well as of hormones and serum proteins, for example, with a very reliable degree of accuracy. Very rapid determinations of blood levels, for example, of theophylline, thyroxine, gentamycin, diphenylhydantoin, digoxin, human growth hormone and IgG in humans may be carried out by relatively simple flow-through procedures. Those involving fluorescent immunoassay procedures find particular application in connection with the use of the foregoing antibody coated filter membranes. When the latter are to be employed for a specific assay the activated membrane must first be sensitized by reacting the activated membrane with an antiserum to the particular substance being determined.

THEOPHYLLINE IMMUNOASSAY

When the antibody coated filter membrane is to be employed in a flow-through procedure for the determination of theophylline blood levels in human serum, the antibody coated filter membrane must be subjected to a specific treatment step so that it is sensitized and will be able to bind a precise amount of the theophylline present in an unknown serum sample with which it is brought in contact.

For such a test the specific treatment step consists of binding an antitheophylline antiserum, preferably from rabbits, to the antibody coated filter membrane. When the filter membrane is treated in this way it is then able to immunobind a precise amount of the theophylline present in the human serum which is brought into contact with it. It also becomes capable of competitively binding a precise amount of tagged theophylline with which it is also brought into contact during the test procedure. By determining the maximum amount of any tagged theophylline which will immunobind with the sensitized filter membrane as well as the ratio in which the tagged and untagged theophylline immunobind with the particular antiserum employed, and then utilizing these determinations as part of a series of parallel flow-through procedures involving serum samples which may contain known as well as unknown concentrations of theophylline, suitable curves may be constructed and an accurate measurement of the concentration of theophylline in the unknown serum sample may be arrived at.

The theophylline immunoassay procedure is carried out as follows:

A series of small cylindrical flow-through columns are prepared with each column being provided with an interior baffle consisting of a disc-shaped section of the antibody coated filter membrane. This disc is so positioned that any liquid introduced into the column must flow vertically through the filter membrane as it passes from the top to the bottom of the column under gravity flow or under positive or negative pressure. The filter membrane discs are maintained in a wetted state using phosphate buffered saline.

The first column of the series is kept separate from the remaining columns so that it can be used to determine the level or content of non-specific binding substances recognized in a serum sample by the filter membrane under the test protocol employed. If not previously identified and quantified the fact that these non-specific binding substances take up certain binding sites on the filter membrane would cause them to be mistakenly considered to be a theophylline value during the test procedure unless they have previously been recognized and compensated for.

The remaining columns of the series are each treated with a predetermined volume of diluted rabbit anti-theophylline antiserum. This antiserum is obtained from rabbits by procedures well known in the art. The usual procedure involves injecting rabbits with a foreign protein employing a complex of theophylline with a large molecule such as bovine serum albumin as the foreign protein, with the injection also including Freund's adjuvant as an additional component. The introduction of this foreign protein together with Freund's adjuvant acts to produce the desired anti-theopylline antiserum in the rabbit host as a response to the normal immune system to the presence of both this foreign protein and Freund's adjuvant. The titer of the antiserum obtained can vary from rabbit to rabbit but this effect can be minimized by pooling the antiserum.

The amount and concentration of rabbit anti-theophylline antiserum which is passed through the second column and caused to bind the activated filter membrane disc is chosen to be less than the actual binding capacity of the antibody on the disc for the antiserum. In order to determine the maximum amount of antiserum which will bind to the filter membrane disc the amount and concentration of the anti-theophylline antiserum introduced into the third column is so chosen as to be sufficient to saturate the binding capacity of the activated filter membrane disc for the antiserum.

These determinations are used to establish the maximum amount of antiserum the activated disc is capable of binding so that, in practice, the amount of antiserum being placed on the disc during this binding step will not exceed the amount of binding sites available on the activated disc. Knowing the maximum antiserum binding capacity of the antibody coated disc avoids the use of an excess which avoids any loss of the antiserum used due to the inability of the excess antiserum to bind to the filter membrane disc because no more antibody binding sites are available. This improves the precision of antiserum binding.

If an excess of fluoroescently labelled theophylline is now passed through this third column it will bind to the antiserum present on the filter membrane disc. The column is then washed with phosphate buffered saline, the bound labelled theophylline is then eluted from the disc and the degree of fluorescence of the amount of free labelled theophylline which has been eluted is read in a fluorometer. This reading provides or establishes a value for that level of fluorescence which is indicative of the upper limit or maximum theophylline binding capacity of the antiserum on the disc.

Knowledge of the maximum binding capacity of the antibody on the disc for the anti-theophylline antiserum and of the antiserum for the theophylline in any serum sample can be utilized in several ways in developing a flow-through test procedure which will be accurate and efficient.

As a basic consideration of economics, the amount of antibody covalently bound to the filter membrane should be enough to immunobind all of the antiserum which is flowed through the antibody coated filter membrane discs since any excess antiserum would be wasted. The antiserum is considerably more costly than the antibody. Secondly, the amount of antiserum placed on the disc must be sufficient to bind a reproducible and accurately measurable amount of the labeled theophylline which is introduced as the tag whose fluorescence is the means by which the amount of theophylline in the unknown serum is quantitated.

When testing the serum of a patient on theophylline therapy for its theophylline blood level, the effective or therapeutic blood level normally encountered will be well below that quantity which the amount of antiserum bound on the disc by the procedure described above is actually capable of binding. By quantitating the test procedure in the way described aove one can be certain that the filter membrane discs will carry sufficient antiserum so that a reproducible and known amount of theophylline is bound. This amount is less than the amount of labeled theophylline being brought into contact with each of the columns but is sufficient to allow accurate quantitation of the tag.

When a serum sample containing both free theophylline and labelled theophylline is passed through an activated filter membrane disc to which a known amount of theophylline antiserum has been bound, as in the case of the second column described above, both the free and labelled theophylline will bind to the antiserum in a competitive ratio. If a series of serum samples each containing a fixed amount of labeled theophylline but with a varying but predetermined amount of theophylline are passed through a series of activated discs to which theophylline antiserum has been bound and the total theophylline bound is then eluted from the disc following which the level of fluorescence of the total theophylline eluted is measured, an accurate curve can be developed from which the theophylline content of any unknown clinical serum sample may be accurately measured since it will be a function of the level of fluorescence which is determined.

Since the maximum degree of fluorescence which can be read is that value which is determined upon elution of bound theophylline when all of the available antiserum binding sites have been occupied solely by labelled theophylline, the ratio of maximum fluorescence thus established to that actually read in the case of an unknown serum sample together with the curve constructed with serum samples containing a known amount of labeled theophylline and known amounts of theophylline, provide all of the information necessary for determining serum theophylline levels in unknown clinical serum samples.

Blood serum level determinations for other substances are carried out by procedure similar to that described above for theophylline.

For example, when carrying out a fluorescent immunoassay to determine the blood serum level in a patient for the antibiotic gentamicin, the activated filter membrane is coated with an anti-gentamicin antiserum obtained, usually, from rabbits and the competitive binding is effected with fluorescently labeled gentamicin. Digoxin blood levels are determined with an activated filter membrane coated with an anti-digoxin antiserum from rabbits, for example, and the test carried out with fluorescently labeled digoxin as the tagged material in the competitive binding. Again diphenylhydantoin blood levels are readily determined by bonding an anti-diphenylhydantoin antiserum to the activated filter membrane and using this membrane for the flow through procedure with fluorescently labeled diphenylhydantoin. By utilizing an anti-thyroxine antiserum and fluorescently labeled thyroxine, very accurate determinations of thyroxin blood levels are obtained.

The activated filter membranes of this invention exhibit low protein affinity and relatively low non-specific binding affinities. In addition, the very high surface area they provide give them the capacity of a relatively long column even though they are of relatively shallow depth.

When the sodium methoxide and trichlorotriazine treated membrane is incubated in a solution of an amine containing antigen, this antigen is covalently bound to the internal surface of the membrane.

These antigen coated membranes are employed to detect specific human antibodies induced by infections, such as hepatitis. Hepatitis surface antigen on the disk surface is contacted with a serum sample by passing it through the membrane. Anti-hepatitis antibodies contained in the sample are bound to the antigens on the membrane. A rinse solution is passed through the membrane, followed by radiolabeled rabbit anti-human IgG antibody. This radiolabeled antibody binds to the human antibodies on the membrane and are quantitated by gamma counting after rinsing.

Antigens such as human IgG can be quantitated by incubating the serum sample with a known amount of radiolabeled rabbit anti-human IgG in solution. The amount of this radiolabeled rabbit anti-human IgG antibody employed is slightly more than that required to completely react with the highest sample IgG concentration expected to be encountered in the serum sample. The mixture of the serum sample and the radiolabeled rabbit anti-human IgG antibody is then passed through an antigen (IgG) coated membrane, allowing the unreacted labeled antibody remaining in the mixture to bind to the membrane. After rinsing, the radioactivity of the membrane to which the labeled but unreacted antibody binds is related to sample concentration through comparison to a standard curve constructed by employing samples of known IgG concentration. This is another useful application of these filter membranes.

We claim:

1. In a method for the preparation of an activated solid phase substrate for use in immunoassay procedures, the steps which comprise treating a dry microporous filter membrane having a cellulose ester base with an alkali metal methoxide in an organic solvent medium to hydrolyze at least some of the ester groups present and convert some of the free hydroxy groups thus made available to the alkali metal hydroxylate form, reacting the alkali metal hydroxylate groups of the cellulose ester with trichlorotriazine, and then removing any residual organic solvent from the solid reaction product.

2. A substrate prepared in accordance with claim 1 and coated with an antibody covalently bonded to the trichlorotriazine moieties on said substrate.

3. In a method for the preparation of an activated solid phase substrate for use in immunoassay procedures, the steps which comprise treating a dry microporous filter membrane formed of a solid polymeric methanol-swellable material which includes esterified hydroxy groups in its chemical structure with an anhydrous organic solvent containing methanol to swell the polymeric structure, hydrolyzing at least some of the ester groups present and converting at least some of the hydroxy groups thus made available to the alkali metal hydroxylate form, reacting the alkali metal hydroxylate groups on said polymeric material with trichlorotriazine, and then removing any residual organic solvent from the solid polymeric reaction product.

4. A substrate prepared in accordance with claim 3 and coated with an antibody covalently bonded to the trichlorotriazine moieties on said substrate.

5. A substrate prepared in accordance with claim 4 wherein the cellulose ester is cellulose acetate.

6. In a method for the preparation of an activated solid phase substrate for use in immunoassay procedures, the steps which comprise treating a dry microporous filter membrane having a cellulose ester base with an anhydrous organic solvent containing methanol to swell the cellulose ester base material, reacting the swollen cellulose ester base material with sodium methoxide to hydrolyze at least some of the ester groups present and convert some of the free hydroxy groups thus made available to the sodium hydroxylate form, reacting the sodium hydroxylate groups on said cellulose ester with trichlorotriazine, and then removing any residual organic solvent from the solid reaction product.

7. A substrate prepared in accordance with claim 6 and coated with an antibody covalently bonded to the trichlorotriazine moieties on said substrate.

* * * * *